US00PP37769P2

(12) United States Plant Patent
van Dijk

(10) Patent No.: US PP37,769 P2
(45) Date of Patent: Oct. 13, 2026

(54) ***ANTHURIUM* PLANT NAMED 'AN2611859'**

(50) Latin Name: *Anthurium andreanum*
Varietal Denomination: AN2611859

(71) Applicant: ANTHURA B.V., Bleiswijk (NL)

(72) Inventor: Jan van Dijk, Bleiswijk (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 19/559,938

(22) Filed: Mar. 6, 2026

(51) Int. Cl.
*A01H 6/10* (2018.01)
*A01H 5/02* (2018.01)

(52) U.S. Cl.
USPC ..... Plt./365

(58) Field of Classification Search
USPC ..... Plt./263.1, 365
See application file for complete search history.

(56) References Cited

U.S. PATENT DOCUMENTS

PP36,310 P2 * 12/2024 Van Dijk ..... Plt./365

* cited by examiner

*Primary Examiner* — Karen M Redden
(74) *Attorney, Agent, or Firm* — C. Anne Whealy

(57) ABSTRACT

A new and distinct cultivar of *Anthurium* plant named 'AN2611859', characterized by its compact, upright to outwardly arching plant habit; freely clumping growth habit; bushy and dense plants; narrowly ovate to roughly narrowly deltoid dark green-colored leaves; freely flowering habit; inflorescences that are positioned above the foliar plane on sturdy scapes; broadly ovate to roughly reniform spathes that are light green and red in color; and spadices that are purplish pink in color with bright red-colored apices.

2 Drawing Sheets

Figure 1:
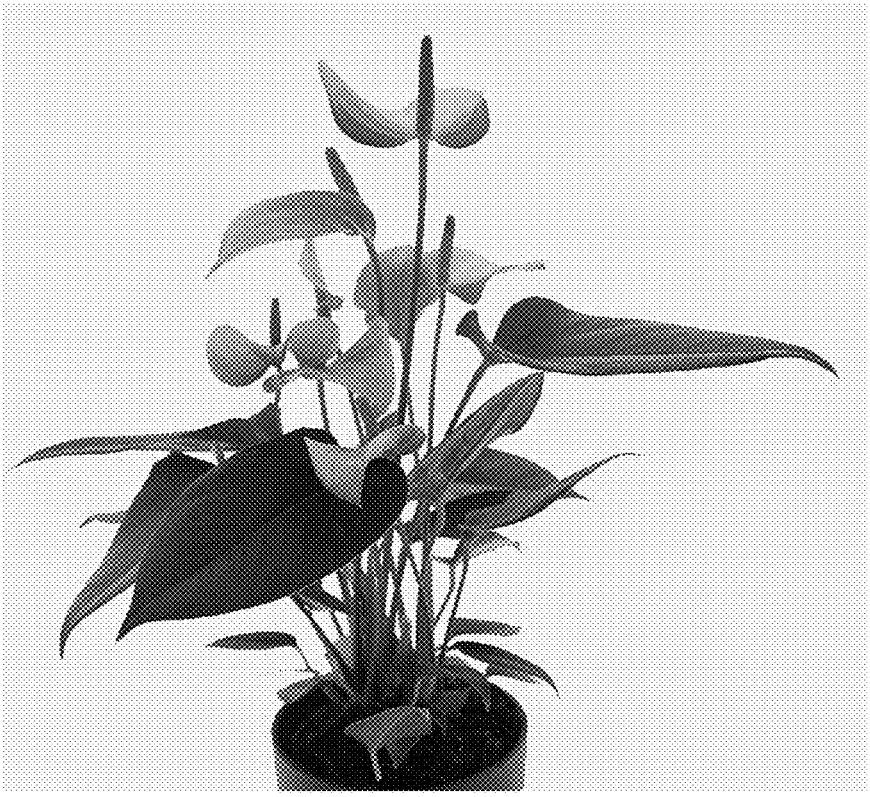

Botanical designation: *Anthurium andreanum.*
Cultivar denomination: 'AN2611859'.

STATEMENT REGARDING PRIOR DISCLOSURES BY APPLICANT

A European Community Plant Breeder's Rights application for the instant plant was filed by the Applicant/Assignee of the instant application, Anthura B.V. of Bleiswijk, The Netherlands on Nov. 20, 2024, application number 2024/2693. Foreign priority is not claimed to this application.

BACKGROUND OF THE INVENTION

The present invention relates to a new and distinct cultivar of *Anthurium* plant, botanically known as *Anthurium andreanum*, commonly referred to as Flamingo Flower and hereinafter referred to by the name 'AN2611859'.

The new *Anthurium* plant is a product of a controlled breeding program conducted by the Inventor in Bleiswijk, The Netherlands. The objective of the breeding program is to create new compact *Anthurium* plants with durable light green and red-colored spathes.

The new *Anthurium* plant originated from a cross-pollination made by the Inventor in January, 2016 in Bleiswijk, The Netherlands of a proprietary breeding selection of *Anthurium andreanum* identified as code number 12-028247-0003, not patented, as the female, or seed, parent with a proprietary breeding selection of *Anthurium andreanum* identified as code number 14-035284-0001, not patented, as the male, or pollen, parent. The new *Anthurium* was discovered and selected by the Inventor as a single flowering plant within the progeny of the stated cross-pollination in a controlled greenhouse environment in Bleiswijk, The Netherlands in July, 2017.

Asexual reproduction of the new *Anthurium* plant by in vitro meristem propagation in a controlled environment in Bleiswijk, The Netherlands since July, 2019 has shown that the unique features of this new *Anthurium* are stable and reproduced true to type in successive generations of asexual reproduction.

SUMMARY OF THE INVENTION

Plants of the new *Anthurium* have not been observed under all possible combinations of environmental conditions and cultural practices. The phenotype may vary somewhat with variations in environment conditions such as temperature and light intensity, without, however, any variance in genotype.

The following traits have been repeatedly observed and are determined to be the unique characteristics of 'AN2611859'. These characteristics in combination distinguish 'AN2611859' as a new and distinct *Anthurium* plant:

1. Compact, upright to outwardly arching plant habit.
2. Freely clumping growth habit; bushy and dense plants.
3. Narrowly ovate to roughly narrowly deltoid dark green-colored leaves.
4. Freely flowering habit.
5. Inflorescences that are positioned above the foliar plane on sturdy scapes.
6. Broadly ovate to roughly reniform spathes that are light green and red in color.
7. Spadices that are purplish pink in color with bright red-colored apices.

Plants of the new *Anthurium* differ primarily from plants of the female parent selection in the following characteristics:

1. Plants of the new *Anthurium* have shorter leaves than plants of the female parent selection.
2. Plants of the new *Anthurium* have smaller spathes than plants of the female parent selection.

Plants of the new *Anthurium* differ primarily from plants of the male parent selection in the following characteristics:

1. Plants of the new *Anthurium* have smaller spathes than plants of the male parent selection.
2. Spathes of plants of the new *Anthurium* are mostly light green in color whereas spathes of plants of the male parent selection are mostly white in color.
3. Spadices of plants of the new *Anthurium* are purplish pink in color with bright red-colored apices whereas spadices of plants of the male parent selection are purple in color with reddish purple-colored apices.

Plants of the new *Anthurium* can also be compared to plants of *Anthurium andreanum* 'AN2884386', disclosed in U.S. Plant Pat. No. 35,188. In side-by-side comparisons, plants of the new *Anthurium* differ primarily from plants of 'AN2884386' in the following characteristics:

1. Plants of the new *Anthurium* have larger spathes than plants of 'AN2884386'.
2. Spadices of plants of the new *Anthurium* are purplish pink in color with bright red-colored apices whereas spadices of plants of 'AN2884386' are purplish red in color with red-colored apices.
3. Scapes of plants of the new *Anthurium* are not tinged with anthocyanin whereas scapes of plants of 'AN2884386' are strongly tinged with anthocyanin.

BRIEF DESCRIPTION OF THE PHOTOGRAPHS

The accompanying photographs illustrate the overall appearance of the new *Anthurium*. The photographs show the colors as true as it is reasonably possible to obtain in colored reproductions of this type. Colors in the photographs may differ slightly from the color values cited in the detailed botanical description which accurately describe the colors of the new *Anthurium*.

The photograph on the first sheet (FIG. 1) is a side perspective view of a typical plant of 'AN2611859' grown in a container.

Figure 2:
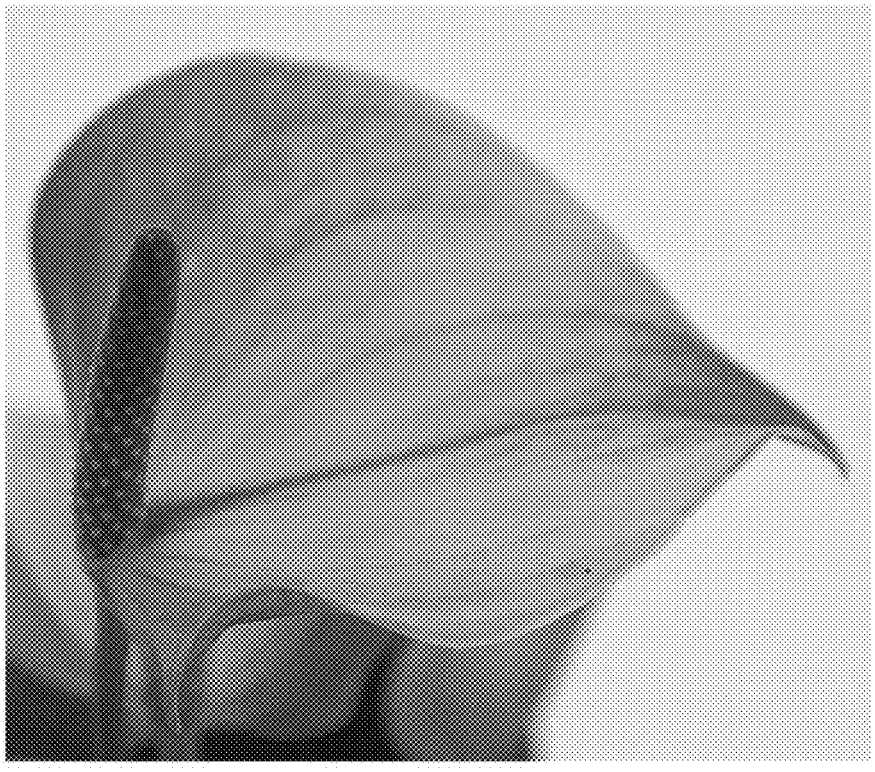

The photograph on the second sheet (FIG. 2) is a close-up view of a typical inflorescence of 'AN2611859'.

DETAILED BOTANICAL DESCRIPTION

The aforementioned photographs and following observations and measurements describe plants grown in 9-cm containers during the early autumn in a glass-covered greenhouse in Bleiswijk, The Netherlands. Plants were grown under conditions and practices which approximate those generally used in commercial *Anthurium* production. During the production of the plants, day and night temperatures ranged from about 19° C. to about 22.5° C. and light levels ranged from about 100 μmol to about 200 μmol. Plants were nine months from planting young rooted plants when the photographs and the detailed description were taken. In the following description, color references are made to The Royal Horticultural Society Colour Chart, 2015 Edition, except where general terms of ordinary dictionary significance are used.

Botanical classification: *Anthurium andreanum* 'AN2611859'.

Parentage:

*Female, or seed, parent*.—Proprietary breeding selection of *Anthurium andreanum* identified as code number 12-028247-0003, not patented.

*Male, or pollen, parent*.—Proprietary breeding selection of *Anthurium andreanum* identified as code number 14-035284-0001, not patented.

Propagation:

*Type*.—By in vitro meristem propagation.

*Time to initiate roots, summer and winter*.—About two weeks at temperatures ranging from about 19° C. to about 22.5° C.

*Time to produce a rooted young plant, summer and winter*.—About six to eight weeks at temperatures ranging from about 19° C. to about 22.5° C.

*Root description*.—Medium in thickness, fibrous; typically creamy white in color; actual color of the roots is dependent on substrate composition, water quality, fertilizer type and formulation, substrate temperature and physiological age of roots.

*Rooting habit*.—Freely branching, medium density.

Plant description:

*Plant shape*.—Compact, upright to outwardly arching plant habit; overall shape, broadly rhomboidal to broadly obovate.

*Growth habit*.—Freely clumping habit imparting a bushy and dense appearance; in a single year of production, about 40 individual plants can be harvested per plant; moderately vigorous growth habit and moderate growth rate.

*Plant height, from soil level to top of leaf plane*.—About 17.5 cm.

*Plant height, from soil level to top of inflorescences*.—About 25.8 cm.

*Plant diameter or spread*.—About 29.2 cm.

Leaf description:

*Arrangement*.—Alternate; simple.

*Length*.—About 12 cm.

*Width*.—About 5.8 cm.

*Shape*.—Narrowly ovate to roughly narrowly deltoid.

*Apex*.—Bluntly apiculate with a small mucronate tip.

*Base*.—Truncate.

*Margin*.—Entire; slightly and coarsely undulate.

*Texture, upper and lower surfaces*.—Smooth, glabrous; moderately coriaceous.

*Venation pattern*.—Pinnate.

*Color*.—Developing leaves, upper surface: Close to 143A; mucronate tip, close to 144B. Developing leaves, lower surface: Close to 144A. Fully expanded leaves, upper surface: Close to a blend of NN137A and 147A; narrow marginal edges, close to 143A; mucronate tip, close to 143A tinged with close to 172B; venation, close to 144A. Fully expanded leaves, lower surface: Close to a blend of 144A and 146B; venation, close to 144A.

*Petioles*.—Length: About 10.9 cm. Diameter: Distally, about 2 mm and proximally, about 3 mm. Texture, upper and lower surfaces: Smooth, glabrous. Color, upper and lower surfaces: Close to 144A. Geniculum length: About 1.4 cm. Geniculum diameter: About 3 mm. Geniculum texture, upper and lower surfaces: Smooth, glabrous. Geniculum color, upper surface: Close to a blend of 144A and 146B. Geniculum color, lower surface: Close to 144A. Wing length: About 2.1 cm. Wing diameter: About 4 mm. Wing texture: Smooth, glabrous. Wing color, upper and lower surfaces: Close to 145A; towards the margins, close to 145C.

Inflorescence description:

*Inflorescence arrangement and flowering habit.*—Spathes with spadices; open inflorescences held above the foliar plane on sturdy scapes; flowering structures arise from leaf axils; freely and continuous flowering year-round in controlled temperature greenhouses in The Netherlands; typically about eight developing and developed inflorescences per plant at one time; inflorescence development commences about 2.5 to 3.5 months after planting rooted young plants.

*Inflorescence longevity.*—On the plant, depending on temperature, spathes maintain good substance for about two months; inflorescences persistent.

*Fragrance.*—None detected.

*Spathes.*—Length: About 6.2 cm. Width: About 6 cm. Shape: Broadly ovate to roughly reniform; moderately concave. Apex: Acute to abruptly acute with a short mucronate apex. Base: Truncate. Margin: Entire; coarsely undulate. Aspect: About 100° from the scape axis. Texture, upper and lower surfaces: Smooth, glabrous; moderately coriaceous. Color: When developing, front surface: Close to 157C; towards the base, close to 143A; towards the apex, close to 53B and 53C; main vein and adjacent secondary venation, close to 53C. When developing, rear surface: Close to 157C and 157D; towards the base, close to 143C; distal margins, close to 53B; main vein, close to 54A. Fully developed, front surface: Close to 157B to 157D; towards the base, close to 143A with proximal margins, close to 141A; towards the apex, close to 53B to 53D with distal margins, close to 53A; main vein and adjacent secondary venation, close to 53B; with subsequent development, colors becoming closer to 145D, 157C and 157D, towards the base, closer to 141B and 143A, towards the apex, tinged with close to 50A and 50B, main vein, closer to 51D and secondary venation, closer to 143A and 143B. Fully developed, rear surface: Close to 157C to 157D; towards the base, close to 143C; towards the apex, close to 54C; margins, close to 53B; main vein and adjacent secondary venation, close to 53C and 53D; with subsequent development, colors becoming closer to 145C, towards the base, closer to 146D, narrow distal margins, close to 51D; main vein, closer to 148B; areas adjacent to main vein, closer to 50D and secondary venation, closer to 147A.

*Spadices.*—Length: About 3.3 cm. Diameter: About 7 mm. Shape: Cylindrical, slightly tapering towards the apex; apex, obtuse; base, obtuse; in cross-section, rounded. Aspect: Erect to about 20° from the scape axis. Color, immature: Close to 47B; towards the apex, close to 48A. Color, mature: Close to 55A; towards the apex, close to 47A. Flowers: Type: Hermaphroditic. Quantity per spadix: About 200. Height: About 1 mm. Diameter: About 2 mm. Shape: Roughly square. Anther color: Close to 55A. Pollen amount: Moderate. Pollen color: Close to 158C. Stigma color: Close to 158D. Ovary color: Close to 146C and 146D.

*Scapes.*—Length: About 17.1 cm. Diameter: About 3 mm. Strength: Sturdy. Aspect: About 22.5° from vertical. Color: Close to a blend of 143B and 144A; distally, closer to 144A.

*Seed and fruit.*—To date, seed and fruit development has not been observed on plants of the new *Anthurium.*

Pathogen & pest resistance: To date, plants of the new *Anthurium* have not been observed to be resistant to pathogens or pests common to *Anthurium* plants.

Temperature tolerance: Plants of the new *Anthurium* have been observed to be tolerant to high temperatures of about 30° C. and to be hardy to USDA Hardiness Zone 10.

It is claimed:

1. A new and distinct *Anthurium* plant named 'AN2611859' as herein illustrated and described.

* * * * *